United States Patent
Stigh et al.

(10) Patent No.: US 7,052,590 B1
(45) Date of Patent: May 30, 2006

(54) METHOD AND KIT FOR THE MANUFACTURE OF SEPARATION GELS

(75) Inventors: Lena Stigh, Indal (SE); Ronnie Palmgren, Stockholm (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 513 days.

(21) Appl. No.: 10/110,020

(22) PCT Filed: Oct. 12, 2000

(86) PCT No.: PCT/EP00/10037

§ 371 (c)(1),
(2), (4) Date: Jun. 27, 2002

(87) PCT Pub. No.: WO01/29098

PCT Pub. Date: Apr. 26, 2001

(30) Foreign Application Priority Data

Oct. 19, 1999 (SE) .................................. 9903748

(51) Int. Cl.
*G01N 27/26* (2006.01)
*G01N 27/447* (2006.01)

(52) U.S. Cl. ...................... 204/469; 204/470
(58) Field of Classification Search ........ 204/450–470, 204/600–621; 522/1–70
See application file for complete search history.

(56) References Cited

U.S. PATENT DOCUMENTS

| | | | | |
|---|---|---|---|---|
| 3,948,743 | A * | 4/1976 | Monthony et al. | 204/469 |
| 4,094,832 | A * | 6/1978 | Soderberg | 526/238.22 |
| 4,721,734 | A * | 1/1988 | Gehlhaus et al. | 522/8 |
| 5,290,411 | A * | 3/1994 | Zewert et al. | 204/606 |
| 6,117,293 | A * | 9/2000 | Zhang et al. | 204/455 |

FOREIGN PATENT DOCUMENTS

| | | | |
|---|---|---|---|
| EP | 0 087 995 A1 | 9/1983 | |
| JP | 08015222 | * 1/1996 | ............ 204/470 |
| WO | WO 97/26071 A1 | 7/1997 | |
| WO | WO 98/28352 A1 | 7/1998 | |

OTHER PUBLICATIONS

"Applications: Free Radical Initiators" Brochure from Aldrich. pp. 5-18.*

Haimo, KK: "N-Vinylcarboxamide-type polymer gels for electrophoresis, their preparation, and an electrophoresis method" STN International, File CAPLUS, CAPLUS accession No. 1996:231562, Document No. 124:283711 JP,A2,08015222,19960119.

Akashi, M., et al.: "Novel hydrogels for electrophoresis" STN International, File CAPLUS, CAPLUS accession No. 1995:136662, Document No. 122:182485 Kuromatogurafi (1994), 15(2), 108-9.

Akashi, M., et al.: "Capillary electrophoresis apparatus" STN International, File CAPLUS, CAPLUS accession No. 1997:614432, Document No. 127:230346 JP,A2,09236580, 19970909.*

Showa Denko KK: "Preparation of N-vinylcarboxylic acid amide-based copolymers in low cost" STN International, File CAPLUS, CAPLUS accession No. 1997:279138, Document No. 126:277907 JP,A2,09059309,19970304.*

* cited by examiner

Primary Examiner—Nam Nguyen
Assistant Examiner—Jeffrey Barton
(74) Attorney, Agent, or Firm—Yonggang Ji

(57) ABSTRACT

A method for the manufacture of a separation gel, which comprises the steps: (i) providing a polymerization mixture containing a first monomer (I) having a polymerizable unsaturated structure and a second monomer (II) comprising two or more polymerizable unsaturated structures and an initiator, and (ii) polymerizing the mixture. The method is characterized in that monomer (I) is an N-vinyl carboxamide; and that (a) the initiating system for the polymerization comprises a UV photoinitiator and polymerization is initiated by UV irradiating the mixture at a wave-length appropriate for the initiator, and/or (b) preselecting monomer (I) and monomer (II) to have comparable reactivities to become incorporated into the growing polymer. A kit for use in the production of an electrophoretic gel is also described. The kit comprises: (a) a monomer (I) carrying an N-vinyl carboxamide group; (b) a monomer (II) carrying a polymerizable unsaturated structure; and (c) an UV initiator compound, a buffer and/or a denaturing agent; said monomers (I and II) being selected to provide comparable reactivities.

6 Claims, No Drawings

METHOD AND KIT FOR THE MANUFACTURE OF SEPARATION GELS

This application is a national stage entry of International Application PCT/EP00/10037, filed on Oct. 12, 2000, and claims foreign priority to Swedish Application 9903748-3, filed on Oct. 19, 1999.

TECHNICAL FIELD

The present invention relates to a method for preparing separation gels. This kind of gels may be used for the separation of various kinds of molecules, such as biomolecules, e.g. by chromatographic methods or electrophoresis, in particular gel electrophoresis and capillary electrophoresis (CE).

In gel electrophoresis the mass transport takes part in a gel while in capillary electrophoresis (CE) the mass transport is in the central channel of a capillary coated with a hydrophilic material.

BACKGROUND ART

Gel electrophoresis is a widely used method for separating biomolecules, such as proteins, peptides, nucleic acids etc. Gel electrophoresis involves the migration of electrically charged molecules in an electric field. A solution containing biomolecules is placed in contact with a supporting gel, an electric field is applied and the molecules are allowed to migrate on or through the electrophoretic gel. Electrophoretic separation of molecules is based on the difference in charge density of the molecules as well as the sieving effect of the porous gel media. The extent of sieving depends on how well the pore size of the gel matches the size of the migrating molecules.

Separation gels have often been prepared by polymerising monomers comprising one or more polymerisable unsaturated structures (primarily carbon—carbon double bonds), in particular vinyl groups. When monomers having two or more polymerisable unsaturated structures are present in the polymerisation mixture, cross-linked polymers will form. Typically the monomers have been acrylates, methacrylates, acrylamides, methacrylamides, acrylonitrile, methacrylonitrile, if applicable bisforms thereof, etc. In certain cases the monomer has been a polymer (prepolymer) carrying a plurality of unsaturated structures. Typical prepolymers have been selected among polyhydroxypolymers, such as dextran, agarose and other polysaccharides. See U.S. Pat. No. 4,094,832; U.S. Pat. No. 4,094,833; EP 87995; WO 9731026, WO 9726071.

Previous polymerisation systems utilise various kinds of initiators. Typical initiators are chemical and thermal. Thermal initiators are often preferred. They have their best efficiency in the range of 50–90° C. Well-known chemical/thermal initiators are azo compounds (for instance 2,2'-azobis(2,4-dimethylvaleronitrile), azoisonitriles, peroxides (for instance benzoylperoxide), persulphates. One important kind of chemical initiators requires irradiation, for instance V, in order to start a polymerisation. Redox systems have also been used, for instance Fenton's reagent (hydrogen peroxide+$Fe^{2+}$).

There have been problems associated with the production of separation gels. Acryl amides, for instance, are often toxic. This is of particular importance for electrophoretic gels because the customer himself often cast them. Further acrylates and acrylamides are sensitive to hydrolysis. Still further, electrophoretic gels have specific demands on homogeneity and physical stability that sometimes can be problematic to achieve. The amount of residual monomer in the polymer immediately after polymerisation has often been high requiring subsequent washing steps and the like.

Consequently, there is a need for new separation gels, for instance electrophoretic gels, and/or improved methods for the production thereof.

Akashi M et al. (Kuromatogurafi 15(2) (1994) 108–109) have tested a gel obtained by radiation initiated polymerisation of N-vinyl acetamide and a bisform of an acrylate in capillary electrophoresis (CE).

Akashi M et al. (JP application 96-43050 (1996) have tested a separation medium obtained by thermally initiated polymerisation of vinyl amine or N-vinyl acetamide (azobis initiator). Koshiji J. (JP application 94-167484 (1994)) has suggested hydrogels obtained, for instance, by ammonium persulphate initiated polymerisation of N-vinyl acetamide or N-vinyl formamide together with a cross-linker, such as N,N'-metylenebisacrylamide, in gel electrophoresis.

Akashi M et al. (Journal of Polymer Science: Part A: Polymer Chemistry, 31, (1993) 1153–1160) have described hydrogels based on N-vinyl acetamide.

Hashimoto et al. (JP application 95-209781 (1995) have described liquid adsorbents and tackifiers prepared by UV initiated polymerisation of N-vinyl formamide or N-vinyl acetamide together with, for instance, N,N'-butylenebis(N-vinyl acetamide) as cross-linker.

To our knowledge the problem with minimising the residual monomer amount after polymerisation is not discussed in any of these publications. Nor UV initiated polymerisation for the preparation of separation gels as defined above seems to have been described previously.

DISCLOSURE OF THE INVENTION

We have cast cross-linked separation gels, primarily for gel electrophoresis, from N-vinyl carboxamides and found that it is difficult to obtain separation gels that contain sufficiently low amounts of residual monomers. This further stresses the need for improvements. We have found that this drawback can be at least partially neutralised in two different ways:

(a) by selecting monomers that polymerises at comparable rates, and (b) by incorporating an UV photoinitiator in the polymerisation mixture and initiate the polymerization by irradiating the mixture at the appropriate wave-length.

A first aspect of the invention thus relates to a method for the preparation of a separation gel of the kind discussed above. The method comprises the steps (i) providing a polymerisation mixture containing a first monomer (I) comprising a polymerisable unsaturated structure and a second monomer (II) comprising two or more polymerisable unsaturated structures and an initiator, and (ii) polymerising the mixture. The characteristic features are that monomer I is an N-vinyl carboxamide; and that (a) the initiating system for the polymerisation comprises a UV photoinitiator and polymerisation is initiated by UV irradiating the mixture at a wave-length appropriate for the initiator, and/or (b) preselecting monomer I and monomer II to have comparable reactivities to become incorporated into the growing polymer.

By a N-vinyl carboxamide is meant a compound that comprises the structural unit $CH_2=CH-NH-COH$ in which one or more of the hydrogens may be replaced by a organic moiety/group providing an sp³-hybridised carbon directly attached to the rest of the N-vinyl carboxamide compound.

N-vinyl carboxamides to be used as monomer I typically have a low molecular weight, for instance below 5000 dalton, for instance below 2000 dalton. Alkyl groups and/or hydrogens are attached at the carbon—carbon double bond or amide nitrogen or carbonyl carbon. Alkyl groups other than methyl preferably contain non-charged or non-chargeable hydrophilic substituents, such as hydroxy or —(CH₂CH₂O)$_n$H.

In a preferred mode of the invention, monomer I has the formula I:

$$CH_2=CR^3-NR^2-CO-R^1$$

in which $R^1$, $R^2$ and $R^3$ independently are hydrogen or lower alkyl, such as $C_{1-10}$ alkyl, for instance methyl. In case anyone of $R^1$, $R^2$ and $R^3$ is $C_{1-10}$ alkyl it contains one or more of the hydrophilic substituents discussed above. In the preferred monomer I of this kind, the alkyl group is methyl, and at least one of $R^2$ and $R^3$ is hydrogen. The monomers having formula I include the following compounds:

| Compound | $R^1$ | $R^2$ | $R^3$ |
|---|---|---|---|
| N-vinyl formamide | H | H | H |
| N-methylvinyl formamide | H | H | CH₃ |
| N-methyl-N-vinyl formamide | H | CH₃ | H |
| N-vinyl acetamide | CH₃ | H | H |
| N-methyl-N-vinyl acetamide | CH₃ | CH₃ | H |

Monomers of formula I can be synthesised according to methods known in the art, e.g. as described for N-vinyl acetamide by M. Akashi et al. (1993) Journal of Polymer Science: Part A: Polymer Chemistry, Vol 31, pp 1153–1160.

Monomer II has two or more polymerisable unsaturated structures, such as vinyl groups, and can function as cross-linkers. This kind of structure may be illustrated by acrylic acid derived groups (acrylamido or methacrylamido or acrylate or metacrylate etc groups). This kind of cross-linkers may be found among compounds carrying two or more N-vinyl carboxamido groups (with preference for such formamido or acetamido groups) or two or more acrylate or methacrylate groups. Two or more polymerisable unsaturated structures, such as acrylate groups or methacrylate groups, may be linked together via an esterified alcohol containing two or more hydroxy groups, for instance ethylene glykol and oligomerised or polymerised forms thereof, various forms of sugar alcohols, propylene diols, butylene diols etc.

In preferred modes of the invention the polymerisation mixture contains at least one cross-linking compound that provides a monomer I/monomer II reactivity ratio as discussed below.

Prepolymers, for instance a polyhydroxy polymer, of the above-mentioned kind carrying a plurality of N-vinyl carboxamide groups constitute a group of monomers that potentially will function both as monomer I and monomer II. When present in the polymerisation mixture this kind of prepolymers therefore does not imperatively need extra monomers carrying one or two polymerisable unsaturated structures to be present. This kind of N-vinyl carboxamides typically has molecular weights above 2000 dalton, such as above 5000 dalton. The number of monomeric units in a prepolymer may be selected according to the same rules as known for other prepolymers carrying unsaturated structures. See U.S. Pat. No. 4,094,832; U.S. Pat. No. 4,094,833; EP 87995; WO 9731026, WO 9726071. Thus there may be from 5 up to 100 or even more, such as up to 1000, 10000 or 100000 monomeric units in a prepolymer. In the preferred variants, essentially all the N-vinyl carboxamide groups in a prepolymer are identical. The substitution degree with respect to N-vinyl carboxamide groups may be selected according to the same rules as known for other prepolymers carrying polymerisable unsaturated structures. See for instance See U.S. Pat. No. 4,094,832; U.S. Pat. No. 4,094,833; EP 87995; WO 9731026; and WO 9726071.

In order to determine the relative reactivity of two monomers, one often studies how the monomers have been incorporated into the growing polymer chain during polymerisation. The relative reactivity may be expressed in form of a monomer reactivity ratio (monomer I/monomer II). In case the monomers are found randomly over the chain this is reflected in a monomer reactivity ratio that is around 1. In case monomer I predominates, monomer I will have a higher reactivity and the monomer reactivity ratio thus will be greater than 1. In general terms determination of monomer reactivity ratios comprises: Pouring the polymerisation mixture after polymerisation into a solvent, e.g. methanol, and isolating the polymer chains. The composition of the chains can be determined in different ways depending on the particular monomer used, for instance in case of amide monomers by nitrogen analysis. The monomer reactivity ratio can then be calculated from the data obtained by a curve-fitting method. See for instance Lindeman et al., Macromolecules 30 (1997) 4073–4077; Otsu et al., 13 (1975) 505–510; George et al., J. Polymer Sci.: Part A: Polymer Chemistry 28 (1990) 2585–2596).

In the present invention the monomer reactivity ratio (monomer I/monomer II) is typically in the interval 0.2–5, such as in the interval 0.5–2, i.e. the reactivities of monomer I and monomer II are comparable.

Non-comparable reactivities between two monomers may be reflected in an increased amount of residual unpolymerised monomers in the polymerisation product immediately after the polymerisation (measured as amount of a residual monomer relative to the added total amount of the same monomer or of the gel produced.

The amount of a residual monomer should be as low as possible, typically below 0.1 mol-% of the total amount of particular monomer added or below 1% (w/w) of the gel formed.

Monomer I and monomer II should be selected among monomers that upon copolymerisation gives a cross-linked polymer that is swellable in water, i.e. can adsorb water without dissolving itself. The absorbance of water is typical in the interval 10–100 g, with preference for 25–50 g, water per gram dry polymer.

The polymerisation mixture may optionally also comprise polymerisable monomers carrying an unsaturated structure other than those specified for monomer I, for instance be a monovinyl compound such as a monoacryl or a monomethacryl amide, or a monoacrylate or a monomethacrylate ester. Monomer III may be selected to provide a monomer reactivity ratio (monomer I/monomer III) around 1 in the same sense as for monomer I/monomer II.

The polymerisation requires an initiating system, typically comprising an initiator.

The initiator may be selected according to previously known rules. See above. The preferred systems are photoinitiated and comprise an UV photoinitiator that may be activated by irradiating with ultra-violet light (UV). There are two typical kinds of UV photoinitiators: 1) those undergoing intramolecular bond cleavage, for instance acetophenone derivatives with and without release of gases (e.g. nitrogen for azoinitiators), and 2) those undergoing intermolecular H-abstraction, for instance benzephenones, benzils and quinones. Typical initiators are 1-hydroxycyclohexylphenyl ketone (Irgacure 184™), phenyl-2,4,6-trimethylbenzoylphosphinate (Lucrin TPO™), phenyl 2-hydroxy-prop-2-yl ketone (Darocur™), 2-hydroxyethoxyphenyl 2-hydroxy-prop-2-yl ketone (Irgacure™ 2959), azobisisobutyronitrile (AIBN), 2,2'-azobis-{2-methyl-N-[1,1-bis(hydroxymethyl)-2-hydroxyethyl]propionamide}, or 2,2'-azobis-[2-methyl-N-(2-hydroxyethyl)propionamide].

The preferred initiators are UV initiators that act via intramolecular bond cleavage, with preference for those not releasing nitrogen gas (non-azo UV initiators). The drawbacks of azo UV initiators are that they may result in gas bubbles (nitrogen) in the gel. This may disturb reading of the gel after electrophoresis and also its cosmetic appearance. A preferred initiator at the priority filing was phenyl 2-hydroxy-prop-2-yl ketone (Darocur 1173™).

In the polymerisation mixture efficient concentrations of monomer I are typically selected within the interval 1–4 M, with preference for within the interval 2–3.5 M. The efficient concentrations of monomer II (cross-linking compound) are typically found in the interval 20–100 mM, with preference for 25–55 mM. The amount of monomer I relative monomer II is typically found in the interval 50–140 (molar ratio). The amount of monomer I relative monomer II may vary along the intended electrophoretic transportation direction thus enabling the manufacture of gradient gels. Efficient initiator concentrations are typically found in the interval 3–8 mM.

The exact amounts of monomer I, monomer II, initiator etc that will give rise to useful separation gels will depend on the selected monomers and selected initiator and has to be determined from case to case.

The ranges given above refers to cases in which the monomers have low molecular weights as discussed above, i.e. primarily 1, 2 or 3 polymerisable unsaturated structures per molecule.

A second aspect of the invention includes a method for separation of biomolecules on an electrophoretic gel manufactured by the method described above. The invention also includes a separation gel, in particular an electrophoretic gel, obtainable by said method for preparation of separation gels.

In a third aspect, the invention includes a kit for use in the production of an electrophoretic gel, said kit comprising
  (i) a monomer (I) carrying an N-vinyl carboxamide;
  (ii) a monomer (II) carrying a polymerisable unsaturated structure; and
  (iii) optionally an UV initiator compound, a buffer and/or a denaturing agent;

said monomers (I and II) being selected to provide comparable reactivities as defined above.

The monomers (cross-linkers and non-cross-linkers), the initiators, including their absolute and relative amounts, to be included in the kit are apparent from what has been said above in the context of the polymerisation mixture.

A fourth aspect of the invention is a method for manufacture a separation gel as defined above, said method comprising the steps:
  (a) providing a polymerisation mixture comprising the above-mentioned prepolymers carrying a plurality of N-vinyl carboxamide structures as known in the art for previously known prepolymers carrying other kinds of groups having a polymerisable unsaturation (carbon—carbon double bond in particular), and
  (b) polymerising the mixture.

Preferably the prepolymer is a polyhydroxy polymer, for instance having polysaccharide structure. The initiator system is included in the polymerisation mixture and can be any of the initiator systems discussed above. Low molecular weight monomers of the kind discussed above as monomer I, monomer II and/or monomer III without specifically complying with the criteria of comparable reactivities may be included in the polymerisation mixture. See further U.S. Pat. No. 4,094,832; U.S. Pat. No. 4,094,833; EP 87995; WO 9731026; and WO 9726071, all of which are incorporated by reference.

EXPERIMENTAL PART

A. Polymerisation Experiments

A1. Photopolymerisation with N-Vinyl Formamide as Monomer I.

Initiator (0.01 mmol), N-vinyl formamide (monomer 1, (20 mmol, 2 ml) and bisacrylamide (monomer II, 15 mg) were mixed with 2.5 ml water in a small Petri dish and placed under UV light (350 nm) for 10 min. The four initiators used were Irgacure 184™ (1-hydroxycyclohexylphenyl ketone, Ciba-Geigy), AIBN (azobisisobutyronitrile, Merck), VA-080™ (2,2'-azobis{2-methyl-N [1,1-bis(hydroxymethyl)-2-(hydroxethyl]propionamide}, Wako) and VA-086™ (2,2'-azobis[2-metyl-N-(2-hydroxyethyl)propionamide], Wako).

Clear transparent elastic gels were formed with all three azo initiators. The gel with VA-086 as the initiator contains the lowest number of bubbles. Irgacure 184 did not give as good gels as the azo initiators did. The gels when using Irgacure 184 were stickier and the mechanical properties were worse even when increasing the concentration.

A2. N-Vinyl Formamide. Gel Formation with Various Initiators and Various Concentrations of Cross-Linker According to literature Potassium persulphate does not initiate N-vinyl-acetamide polymerization reaction in aqueous solutions as the monomer reacts with the former to give hydrozylates. Benzoyl peroxide is neither a good choice since it is an inefficient initiator of NVA polymerization in protic solvents resulting in low yields. (Kirsh, Y. E. (1998). Radical polymerization. *Water soluble poly-N-vinylamides: Synthesis and Physiochemical properties*: p 36–80.) Persulphates and Benzoyl peroxides are for obvious reasons not tested.

Gel formation with N-vinyl formamide as monomer (I), using various initiators and various concentrations of the cross-linker bisacrylamide (monomer II), was studied. The initiators studied were the same as those mentioned above in Example 1(b).

The gels were prepared as described in Example 1(b) and inspected for quality, number of bubbles, degree of clarity and residual monomers.

The results indicated that the azoinitiator VA-086™ (2,2'-azobis[2-metyl-N-(2-hydroxyethyl)propionamide] gave particularly good results when used at a concentration between 0.5 and 2.5 mM. The optimal initiator concentration seems to be 1 mM and below. A bisacrylamide concentration of between 10 and 40 mm, preferably around 25 mM, was found to be suitable.

A3. N-Vinyl Acetamide. Gel Formation with Various Initiators

The selected initiators were Irgacure 651 (Ciba Geigy), Irgacure 2959, (Ciba Geigy), Darocur 1173 (Ciba Geigy), benzoin ethylether (Aldrich) Quantacure QTX (Ward Blenkeninsop & Co Ltd), methylene blue, Lucirin TPO (BASIS Kemi) together with TEMED (Amersham Pharmacia Biotech) and Darocur 1173 mixed with TEMED plus Lucirin TPO.

In initial testing of the different initiators the polymerisations were made in glass Petri dishes. Monomer I was N-vinyl acetamide and monomer II was bisacrylamide. The concentration of the initiators was varied. The gels were tested for residual monomers, swelling degree and approximate mechanical properties.

Quantacure was promising according to mechanical properties and monomer residues, but gave yellow gels. The lowest amount of monomer residues was found in gels initiated by Darocur 1173. See example 4.

A4. N-Vinyl Acetamide. Polymerisation Adapted to Give Low Amount of Residual Monomer.

N-vinyl acetamide (monomer I, NVA) (Showa Denko, 1,55 ml of 9M), Darocur 1173 (280 µl of 10 0 mM in ethyleneglycol), bisacrylamide (monomer II) (1,0 ml of 120 mM) and milli-Q water are mixed in a Petri dish. The gels are then polymerised by UV-light for 20 minutes. The plates are placed approximate 10 cm under the solarium tubes. The UV-source irradiates with a wavelength of approximate 350 nm.

This leads to a gel recipe with the concentration of 3,5 M N-vinyl acetamide, 30 mM Bisacrylamide and 7 mM Darocur 1173.

The gel produced was tested for residual monomers, swelling degree and mechanical properties.

The gel gave less than 0,1 mole percentage residuals per mole NVA, which is less than 1 weight percentage of gel weight. See part B of the experimental part. A dried gel of the above recipe swelled 38 times by weight after 3 days in excess water.

A5. Gel Formation with Different Kinds of Monomer II (Crosslinkers)

The following crosslinkers have been tested as monomer II:

poly(ethylene glycol) dimethacrylate Mw≈330 (Aldrich)
poly(ethylene glycol) dimethacrylate Mw≈400 (Röhm)
poly(ethylene glycol) dimethacrylate Mw≈550 (Aldrich)
poly(ethylene glycol) dimethacrylate Mw≈875 (Aldrich)
poly(ethylene glycol) diacrylate Mw≈575 (Aldrich)
poly(ethylene glycol) dimethacrylate Mw≈330 (Aldrich)
1,4-bis(acryloyl)piperazine (Fluka)
pentaerythritol triallyl ether (Aldrich)
divinylglycol (Polysciences Inc.)
glycerol dimethacrylate (Aldrich)

Polymerisation has been performed in a similar way as in A3 and A4.

Varied parameters have been the concentration of crosslinker, concentration of N-vinyl acetamide and concentration of the initiator Darocur 1173. The gels were analysed by HPLC and electrophoresis. The most promising gel is obtained with poly(ethylene glycol) dimethacrylate and poly (ethylene glycol) diacrylate as monomer II. The other crosslinkers gave higher levels of monomer residues or lower mechanical strength in performed experiments.

The mechanical properties are as good as a polyacrylamide gel and the gels transparent.

Preferred concentrations in the polymerisation mixtures are 2–3,5 M of N-vinyl acetamide (monomer I), 25–55 mM of crosslinker and 3–7 mM of initiator.

This gives gels that swell 25 to 50 times their weight in excess water for 3–5 days.

A6. Polymerisation of Gels for Electrophoresis

When polymerisation of a gel for electrophoresis, the polymerisation mixture typically includes a buffer. In this example a tris buffer is chosen.

The quality of the glass plates is important. It should not absorb too much of the required wavelength. For vertical gel electrophoresis the glass plates with spacers are mounted in a Dual gel caster.

N-vinyl acetamide (2666 µl of 9 M), Darocur 1173 (84 µl of 1 M in ethyleneglycol), bisacrylamide (1666 µl of 120 mM), Trisbuffer (2000 µl of 1,5 M) and milli-Q water (1584 µl) are mixed. The cassette is filled with the gel solution from above. The comb is then placed on top and the gel is polymerised by UV-irradiation for 20 minutes.

Besides electrophoresis the gel was tested for hydrolysis and residual monomers.

B. Functional Testing Protocols and Analytical Protocols for Testing Residual Monomers and Stability Against Hydrolysis.

B1. Electrophoresis in a Poly-N-Vinyl Formamide Gel

A poly-N-vinyl formamide gel was prepared by mixing 375 µl VA-086™ (50 mM in water); 2.3 ml bisacrylamide (20 mg/ml); 4.5 ml conc. N-vinyl formamide; 3.1 ml Tris-HCl (1.5 M, pH 8.6); and 2.1 ml water. A standard polyacrylamide gel was prepared for comparison. Both gels were polymerised in plastic cassettes by initiation with UV light (350 nm) for 10 min. The poly-N-vinyl formamide gel was equally clear and transparent to the polyacrylamide gel.

The gels were loaded with prestained molecular weight marker proteins (4 to 250 kDa) and run at constant current (20 mA per gel) for 52 minutes and standard denaturing conditions. The gels were scanned immediately after electrophoresis.

The results indicated that the separating properties of the poly-N-vinyl formamide were equal to the standard polyacrylamide gel. There was a separation of protein bands corresponding to marker proteins from 16 to 105 kDa.

B2. Electrophoresis in a Poly-N-Vinyl Acetamide Gel

A poly-N-vinyl acetamide gel was prepared by mixing 270 µl VA-050™ (50 mM in water); 2.1 ml bisacrylamide (120 mM); 3.5 ml N-vinyl acetamide (9 M); 2.25 ml Tris-HCl (1.5 M, pH 8.6); and 0.88 ml water. The gels were polymerised between glass plates by initiation with UV light (350 mm) for 10 min. The poly-N-vinyl acetamide gel was equally clear and transparent to the polyacrylamide gel.

The gels were loaded with prestained molecular weight marker proteins (4 to 250 kDa) and run at constant current (20 mA per gel) for 72 minutes and standard denaturing conditions. The gels were scanned immediately after electrophoresis.

The results indicated that the separating properties of the poly-N-vinyl acetamide were good. There was a separation of protein bands corresponding to marker proteins from 6 to 260 kDa.

B3. Analysis of Monomer Residues by HPLC

A polymerised gel is weighed and placed in a beaker with 120 g of milli-Q water. The beaker is covered with parafilm and left for stirring 3–5 days. A water sample is taken from the beaker and diluted to a suitable concentration. Before injection of the sample a series of dilution of the monomer is prepared and injected at the HPLC.

The HPLC conditions are Isocratic 7% acetonitril with a flow of 1 ml/min and wavelength of 225 nm. The colon is a HP hypersil 5 μm 125*2 mm, 79926 18-562

The percentage of monomer is plotted versus the top area of the standard samples. The equation of the linear correlation is then used to determine the concentration of the sample. The dilution factor, the weight of transferred gel and the weight of added water is then taking into account to determine weight percentage monomer residues of the gel.

B4. Stability Tests of N-Vinyl Acetamide Gels

Six gels were cast according to example A4. The gels were washed with water for several days until there are no monomer residues left according to HPLC. The gels were put into one beaker each with 50 ml of either 0.1 M NaOH, 0.1 M HCl or water and left for one and three days. Acrylamide gels have been treated the same earlier.

The gels were divided into quarters. One quarter of the gels was weighed and homogenised by a hand mixer. 50 ml of milliQ water was added and the mixture was titrated with either 0.1 M NaOH or 0.1 M HCl depending on start pH. Water samples were taken and ran on a LC-MS.

No hydrolysis have occurred in the water samples, acid samples and not after one day in base.

After three days of basic hydrolysis a two step titration curve occurred indicating one hydrolysis product. Possible hydrolysis products are acetic acid and maybe polyvinylamine. LC-MS showed one molecular weight top at 60.2 which supports that acetic acid is the detected hydrolysis product.

Compared to the polyacrylamide gels the N-vinyl acetamide gel is much more resistant to hydrolysis.

What is claimed is:

1. A method for the manufacture of a separation gel, which comprises the steps:
    (i) providing a polymerisation mixture containing a first monomer (I) comprising an N-vinyl carboxamide, having a polymerisable unsaturated structure and a second monomer (II) including two or more polymerisable unsaturated structures and a UV photoinitiator, and
    (ii) polymerising the mixture:
   wherein the monomer I is the same as the monomer II and is a polyhydroxy polymer camming a plurality of N-vinyl carboxamide structures.

2. The method of claim 1, wherein the initiator comprises a UV photoinitiator and polymerisation is initiated by UV irradiating the mixture at a wave-length appropriate for the initiator.

3. The method of claim 2, wherein the initiator is activated through intramolecular bond cleavage.

4. The method of claim 2, wherein the initiator is a non-azo initiator.

5. The method of claim 2, wherein the initiator is a phenyl ketone having a hydroxy substituent at position 2 in relation to the carbonyl group (α-substituent).

6. In a method for the separation of biomolecules on an electrophoretic gel, the improvement comprising preparing said electrophoresis gel by the method of claim 1.

* * * * *